(12) United States Patent
Bargh

(10) Patent No.: US 10,041,030 B2
(45) Date of Patent: Aug. 7, 2018

(54) BIOREACTOR VESSELS AND ASSOCIATED BIOREACTOR SYSTEMS

(71) Applicant: TAP BIOSYSTEMS (PHC) LIMITED, Royston, Hertfordshire (GB)

(72) Inventor: Adrian Neil Bargh, Royston (GB)

(73) Assignee: TAP BIOSYSTEMS (PHC) LIMITED, Royston, Hertfordshire (GB)

( * ) Notice: Subject to any disclaimer, the term of this patent is extended or adjusted under 35 U.S.C. 154(b) by 553 days.

(21) Appl. No.: 14/417,739

(22) PCT Filed: Jul. 29, 2013

(86) PCT No.: PCT/GB2013/052029
§ 371 (c)(1),
(2) Date: Jan. 27, 2015

(87) PCT Pub. No.: WO2014/020327
PCT Pub. Date: Feb. 6, 2014

(65) Prior Publication Data
US 2015/0307828 A1    Oct. 29, 2015

(30) Foreign Application Priority Data
Jul. 30, 2012    (GB) .................................. 1213506.7

(51) Int. Cl.
*C12M 1/00* (2006.01)
*C12M 3/00* (2006.01)
(Continued)

(52) U.S. Cl.
CPC ............ *C12M 23/40* (2013.01); *C12M 21/00* (2013.01); *C12M 23/02* (2013.01); *C12M 23/26* (2013.01);
(Continued)

(58) Field of Classification Search
CPC .............................. C12M 23/42; C12M 23/40
See application file for complete search history.

(56) References Cited

U.S. PATENT DOCUMENTS 5,026,650 A * 6/1991 Schwarz ................ C12M 23/24
261/83
5,994,129 A    11/1999 Armstrong et al.
(Continued)

FOREIGN PATENT DOCUMENTS

EP    2130904 A2    12/2009
EP    2251407 A1    11/2010
(Continued)

*Primary Examiner* — Jonathan M Hurst
(74) *Attorney, Agent, or Firm* — Dickinson Wright PLLC

(57) ABSTRACT

A bioreactor vessel (100) is provided with a rigid ledge projecting to a side thereof and defining fluid conduits (136a-c) between three respective externally-facing ports (132a-c) and a vessel chamber (105). A bioreactor system includes a cell culture module (10) having a receiving station (14) in which the vessel (100) is received, in use. Three fluid connection ports (314a-c) are located adjacent to the receiving station (14) and are in fluid connection with associated gas and/or liquid input lines (302a-c, 316, via a valve assembly (300). When the vessel (100) is inserted into the receiving station, the rigid nature of the ledge and the defined positions of the receiving station connection ports (314a-c) mean that the externally-facing ports (132a-c) on the vessel are brought into registration with the receiving station connection ports (314a-c), thereby forming respective fluid connections automatically, without having to manually couple fluid lines on the vessel (100) to ports on the cell culture base (12).

27 Claims, 10 Drawing Sheets

(51) Int. Cl.
*C12M 1/06* (2006.01)
*C12M 1/34* (2006.01)

(52) U.S. Cl.
CPC ............ *C12M 23/38* (2013.01); *C12M 23/42* (2013.01); *C12M 23/44* (2013.01); *C12M 23/46* (2013.01); *C12M 23/48* (2013.01); *C12M 23/58* (2013.01); *C12M 27/02* (2013.01); *C12M 29/00* (2013.01); *C12M 41/00* (2013.01)

(56) References Cited

U.S. PATENT DOCUMENTS

| | | | | |
|---|---|---|---|---|
| 6,673,598 | B1* | 1/2004 | Akers | C12M 23/14 |
| | | | | 435/297.2 |
| 7,682,823 | B1* | 3/2010 | Runyon | C12M 23/14 |
| | | | | 210/616 |
| 2004/0009473 | A1* | 1/2004 | Pease | C12Q 1/66 |
| | | | | 435/5 |
| 2007/0212750 | A1* | 9/2007 | Kieffer | C12M 23/26 |
| | | | | 435/34 |
| 2008/0032396 | A1* | 2/2008 | Chokshi | C12M 23/08 |
| | | | | 435/294.1 |
| 2011/0003323 | A1* | 1/2011 | Bargh | C12M 23/42 |
| | | | | 435/29 |

FOREIGN PATENT DOCUMENTS

| | | | |
|---|---|---|---|
| EP | 2270129 | A2 | 1/2011 |
| WO | 2004/106484 | A2 | 12/2004 |
| WO | 2006/119622 | A1 | 11/2006 |
| WO | 2011/090781 | A1 | 7/2011 |

* cited by examiner

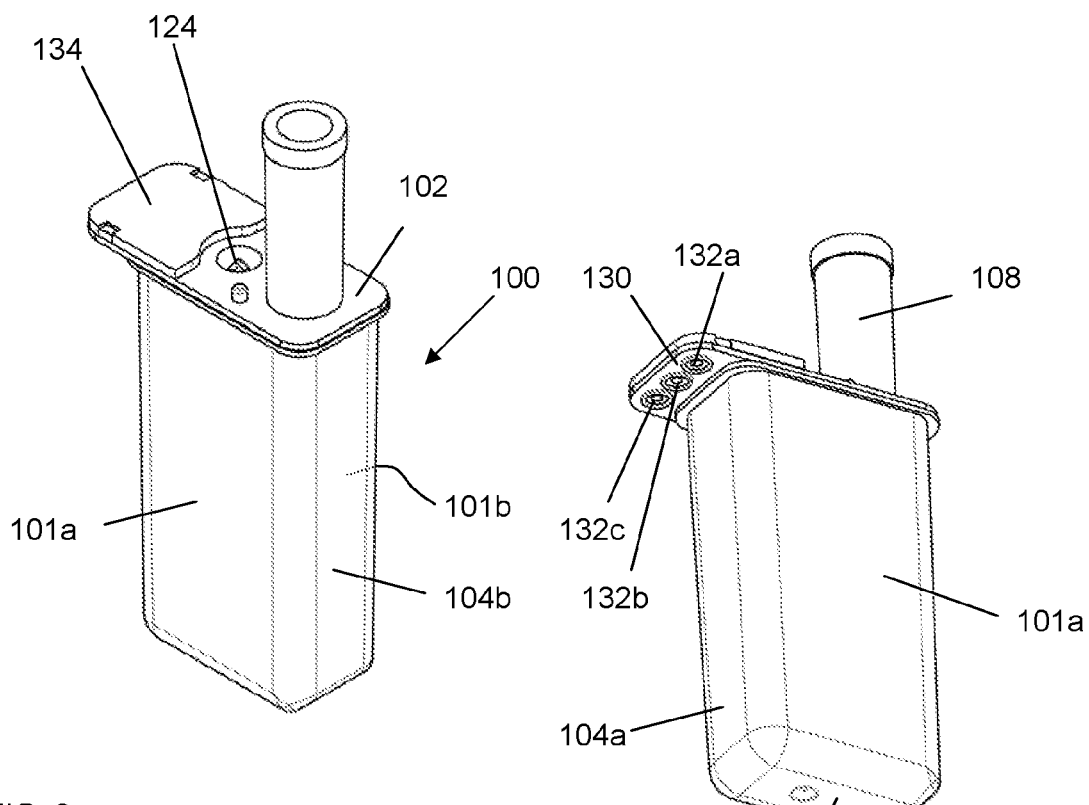
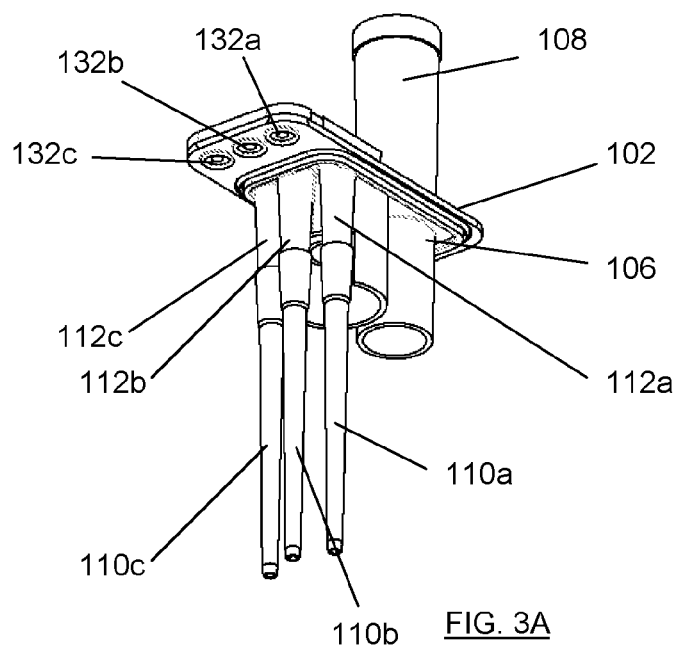

BIOREACTOR VESSELS AND ASSOCIATED BIOREACTOR SYSTEMS

FIELD OF THE INVENTION

The invention relates generally to the field of bioreactor processing systems for suspension cell cultures. More particularly, the invention concerns improvements to bioreactor vessels for insertion into cell culture modules within bioreactor systems and to improved methods of processing those bioreactor vessels.

BACKGROUND TO THE INVENTION

Cell cultures, consisting of cells growing suspended in a growth media, or on the surface of suspended particles, in solution are produced within bioreactors with careful control of a number of parameters. These bioreactors may be capable of processing large quantities of cell culture solution. For example, large-scale bioreactors can have capacities from 1-20,000 liters, or even up to 50,000 liters.

Within the bioreactor it is important to carefully control the environment to which the cells are exposed. Subtle changes in the environment can have major effects on the physiology of the cells and the amount of the target product (product titre), for example a recombinant protein, that is produced by each cell. This in turn has a major impact on the economics of the production process. The parameters that must be controlled include the concentrations of oxygen and carbon dioxide available to the cells (dissolved oxygen and $CO_2$), pH, temperature, and specific nutrient levels such as the concentration of glucose. Additionally the physical environment is critical; particularly important components including the form of the gas distribution e.g. bubble size and overall gas flow. Finally, the mixing of the liquid and cells is critical having an impact on the homogeneity within the reactor and hence the local environmental variation to which cells within a bioreactor are exposed. Such issues become significant in very large bioreactors.

A major challenge facing companies manufacturing products in bioreactor systems is the optimisation of the conditions within a bioreactor for the production of a particular product. Optimisation of conditions for a particular cell line producing a particular product can easily have magnitude level effects on the yield of the product, this in turn having a massive impact on the economics of production. Addressing this issue is not simple; there are many parameters to be controlled and the optimal approach may involve variations in these conditions over time. However, it is impractical to explore the impact of varying a range of parameters due to the lack of availability of equipment and the huge costs of operation. The actual costs of one run of a 2l bioreactor can be over $2000. At larger scales the cost rapidly becomes prohibitive. Such issues prevent the application of modern statistical based experiment approaches to resolving the impact of multiple parameter variation typically referred to as DOE (Design of Experiment), such approaches typically requiring tens of bioreactor experiments to have value.

The opportunity for such work to have value has increased over recent years as regulatory authorities have introduced initiatives in which variations within a production run do not necessarily mean the automatic failure of a batch if the impact of such variations in control parameters has previously been explored. This is impossible without small-scale highly parallel models of bioreactors, but is essential for manufacturers to remain competitive.

A further issue faced by bioreactors is the difficulty of selecting cell lines early in development that are robust and productive in a stirred bioreactor environment. Clearly, where high tens to hundreds of cell lines need to be screened, existing bioreactor systems are impractical.

A number of small-scale approach bioreactors have been tried, e.g. shaken multiwell plates and flasks, but these lack the ability to faithfully reproduce the conditions found in stirred, gassed systems with closed loop control of culture parameters. To date, small-scale experiment runs are generally carried out in individual bioreactors, of 1 to 10 liter capacity, containing cell cultures in solution. These are processed under careful, monitored control for a period of about two weeks for mammalian cultures; microbial cultures are typically processed for shorter durations. During that period, the input parameters discussed above may be varied between the individual bioreactors, with the contents of the respective bioreactors being monitored so as to determine which set of parameters achieves optimum, desired results. That set of parameters can then be used in order to scale-up the process to full production scale; the objective being to maximise cell production or cell viability, to improve production efficiency and/or to increase product titre yield.

Control of the culture parameters is required from three perspectives: i) the maintenance of a parameter at a defined set-point, within control limits, for a given time; ii) the controlled, planned variation of that parameter over time; and finally iii) the consistency and reproducibility of that parameter from bioreactor to bioreactor and run to run. Once such control is achieved, parameters can be varied and the impact of the variation on productivity determined.

The cell culture solution within a bioreactor may be stirred in order to ensure homogeneity. The rate of stirring can have a major impact on the productivity of the culture through the impact of the physical environment of the cells, for example shear, on the viability and productive life of the cells. Additionally, the stirring rate has a direct effect on mixing and therefore the efficiency of mass transfer of gasses from the input stream of bubbles into the liquid phase where it is available to the cells. The balance between stir rates and their potential negative effects and the benefits of good mixing and gas transfer must be established for a particular culture. At manufacturing scale, energy inputs to the reactor additionally become an important economic consideration.

In many existing small-scale systems, the contents of the bioreactor vessels are not stirred, but are instead agitated by shaking. Whereas this simplifies the system, the vessels not requiring individual stirrers, it does not produce accurate simulation of production scale conditions, in which the contents are stirred; shaking does not replicate the shear forces induced in the vessel contents by stirring. Additionally, gas transfer in shaken vessels is primarily through surface aeration rather than bubbles fed into the base of the system, altering the dynamics of the gas transfer and the physical environment.

Where stirrers are provided, each is typically independently driven from a drive source. It is time-consuming for the operator to connect and disconnect each stirrer to the associated drive source, as is required between experiment runs. In EP2270129, there is disclosed a system and associated method for connecting a plurality of stirrers of respective small-scale bioreactors in a single action through a common drive plate.

There are two key aspects to the gas control within bioreactors: that of $CO_2$ and that of $O_2$.

The dissolved oxygen level in the bioreactor must be maintained at a set level to ensure a consistent availability to the cells such that metabolism is not limited. Typical maintenance levels vary between 15 and 50% of the maximum dissolved oxygen level achieved by air saturation. Approaches to achievement of this vary between users, some preferring to use lower input concentrations and higher flow rates, others higher input concentrations and lower flow rates. Control of the input flow rate is critical as it affects the stripping of other gases such as $CO_2$ from the culture media.

The concentration of $CO_2$ that the cells are exposed to can have significant effects on metabolism, particularly in mammalian cell cultures. For such mammalian cultures, control of $CO_2$ can therefore additionally be used to control pH in combination with bicarbonate based buffer systems in the media. Bubbles are also a key source of damage to cells and hence control of the total gas inflow rate is an important factor in maintaining cell viability.

The pH level within the bioreactor should remain within predetermined bounds, which can vary as the cell culture develops. In mammalian cell cultures, this is achieved by a combination of a bicarbonate based buffer system within the liquid media, combined with the maintenance of a specific level of dissolved $CO_2$. However, above a certain cell density the production of lactic acid by the cells can overwhelm the buffering capability of the media and the pH is maintained within the desired limits by the addition of doses of alkali solutions to combat the increasing acidity. The addition of alkali in bioreactors is controlled as part of a feedback loop including a pH sensor.

Temperature is an important parameter within bioreactors. The temperature used within bioreactors culturing mammalian cells does not vary widely due to the origins of the cells in animals exhibiting control of body temperature. However, some minor variations are used during the period of culture, to effect shifts in metabolism biasing the cell physiology towards production of the recombinant protein rather than cell multiplication for example. For microbial cultures, the operating temperature may vary, dependent on the organism, between 18-65° C. and needs to be controlled accurately.

Generally, a heater is controlled in order to increase or decrease the amount of supplied heat. In some systems the culture growth and energy inputs into stirring generate excess heat, so cooling and heat dissipation systems are required.

A range of nutrient feeds may be dispensed into the reactor. Typically these include media feeds which supply additional amino acids and carbon sources to replace those used in cell growth. Multiple different feeds may be added to a bioreactor on different schedules, often including carbon sources such as glucose. Generally, such feeds are added in response to the measurement of parameter levels within the bioreactor.

It is time-consuming and often manually complex for an operator to connect and disconnect the fluid conduits to the respective inlet/outlet ports so as to establish the fluid pathways for the input of gases and/or nutrients into the bioreactor vessel.

Monitoring of various parameters within the bioreactor is key to their control. Some parameters are controlled through closed loop sensing and response systems, others through sampling and off-line analysis due to the lack of appropriate on-line monitoring systems.

The monitoring of the vessel contents may be achieved by 'invasive' methods in which a small sample portion of the cell culture solution is removed for at-line or off-line analysis, for example via sampling port or by aspirating a sample of the solution with a pipette for dispensing for example into the sample cup of an analytical system. Likewise, a sample portion of the gases in the headspace within the vessel may be extracted for analysis in, for example, a gas analyser. That extraction may be done by a probe inserted into the headspace, or via a gas outlet port and associated conduit. As with the connection of the fluid conduits for the input of gases or nutrients into the vessel, where the liquid samples and/or the headspace gases are analysed via extraction through an outlet port in each vessel, it is time-consuming and often manually complex for an operator to connect and disconnect the fluid conduits to the respective outlet ports, a primary risk being the contamination of the device to be inserted. Such problems add to the general complexity and cost of conducting multiple bioreactor experiments.

In EP2270129, the process was improved by enabling the connection of multiple fluid pathways in a single step through use of a common clamp plate defining respective conduits between the inlet/outlet ports of the respective vessels and associated fluid ports in a base station. However, a drawback of this approach is that fluids can remain in the conduits of the clamp plate between experiment runs, risking contamination of subsequent runs—particularly in the case of the nutrient feed. This problem may be overcome by flushing out and/or sterilising the conduits between runs, but that adds an additional step to the process.

In summary, there is a range of challenges in the development and optimisation of bioreactor based manufacturing processes, including: i) general costs of operation of current systems, even that of small scale systems being prohibitive due to complexity of set-up, labour, capital cost, equipment availability within facilities infrastructure required (steam generation) and high costs of media components per unit volume; ii) lack of directly applicable small-scale systems to model larger bioreactors; and iii) a lack of trained personnel driving the requirement for improved throughput per trained employee.

Accordingly, it is an object of the invention to improve the ease and efficiency of the turnaround between experiment runs in micro- and macro-scale bioreactor systems, reduce labour requirements, reduce the risk of contamination and increase throughput in laboratories.

SUMMARY OF THE INVENTION

According to a first aspect of the invention, there is provided a bioreactor vessel comprising:
  a chamber defined by top, bottom and side walls;
  a rigid ledge projecting to a side of the vessel and having an externally-facing connection port; and
  a conduit at least partly defining a fluid flow path between the chamber and the externally-facing connection port.

The provision of the sideways-projecting rigid ledge with the externally-facing connection port, and a conduit that is a part of the vessel itself between the chamber and the externally-facing connection port, facilitates the set up of a bioreactor system and improves the efficiency of the turnaround between experiment runs because all that is required to establish a fluid pathway between the interior of the vessel (the chamber) and a corresponding fluid port (such as one in a base station in which the bioreactor vessel is received, for the supply of gases or nutrients) is to insert the vessel in position within a receiving station in the base station. The rigidity of the ledge ensures that the externally-facing connection port on the vessel is brought into registration with a corresponding port in the base station to establish a direct fluid connection. There is no need for an intermediary part defining connecting fluid conduits, and therefore no problems associated with latent fluids in those connecting conduits. There is no need for flushing or sterilisation of the conduits, because the bioreactor vessel would typically be disposed of after a single use.

The conduit may terminate with an open end within the chamber. Alternatively, the chamber may include a chamber port through one of said top, bottom and side walls, the conduit being connected at a chamber end to said chamber port.

In one embodiment, the conduit may be defined internally within the ledge. In this case, the ledge may comprise: a lip projecting to a side of the vessel; and a gallery plate; wherein the externally-facing connection port extends through the lip, and wherein the gallery plate includes a groove extending between the externally-facing connection port and the chamber, thereby defining said conduit. This arrangement provides a simple and robust fluid pathway that is easy to manufacture and therefore inexpensive.

Where the vessel includes a chamber port and the ledge comprises a lip, as above, then the lip may comprise a part of the top wall of the chamber, which also defines the chamber port. The top wall may comprise a lid of the vessel. With such an arrangement, existing bioreactor vessels may be adapted very simply, just by replacing the lid with one having the additional lip feature, and by connection of the grooved gallery plate above the top wall (lid).

Alternatively, where the vessel includes a chamber port and the ledge comprises a lip and a gallery plate, as above, then the lip may instead comprise a part of a side wall of the chamber, and the gallery plate may comprise a part of the top wall of the chamber, which also defines the chamber port. Such an arrangement would require modification of the existing vessel sidewalls.

In an alternative embodiment, the conduit may be defined externally of the ledge. In this case, the conduit may comprise flexible tubing. This provides a simple and inexpensive connection between the chamber and the exterior. Flexible tubing of the type required for this arrangement is readily available and hence this arrangement does not require any 'bespoke' parts other than the rigid ledge feature.

No matter which embodiment, the ledge may project from an upper end of the vessel. This is a convenient arrangement for placing the vessel into a cell culture module, because the receiving station in the cell culture module base may be at a lower end thereof to receive the lower end of the vessel, and the port in the vessel to which the externally-facing connection port in the ledge connects may be towards an upper end of the cell culture module base.

Furthermore, the externally-facing connection port may be on a bottom surface of the ledge. Thus, the fluid connection can be established simply by inserting the vessel downwardly into the base. Gravity would assist both the insertion and the maintenance of a seal at the connection between the externally-facing connection port and the associated port in the cell culture module base.

Optionally, the ledge may include a plurality of said externally-facing connection ports, a respective plurality of conduits at least partly defining a respective plurality of fluid flow paths between the chamber and each of said externally-facing connection ports. The plurality of flow paths may comprise a manifold, having a branch to each respective externally-facing connection port stemming from a main conduit. Multiple gases may be supplied from different lines to a common conduit for input to the vessel. Nutrients may be supplied separately, via another fluid flow path, or may be supplied via the same path as the gases. By combining the different flow paths to a common conduit, the vessel need only have a single input—such as the chamber port—to the chamber.

The vessel typically further comprises a tube, an upper end of the tube being connected to the chamber end of the conduit. A tube enables the input gas(es) and/or nutrients to be input directly to liquid in the chamber. Where there are multiple inlet and outlet paths, they may combine to a common conduit, as above, for connection to the tube or one or some may connect to the tube with others opening into the vessel headspace.

According to a second aspect of the invention, there is provided a bioreactor system, including a cell culture module comprising:

a base including a receiving station for removably receiving a bioreactor vessel of the type defined in the first aspect of the invention, the receiving station including at least one receiving station fluid port, such that the or each externally-facing connection port in the ledge is in registration with an associated at least one receiving station fluid port when received in the receiving station; and means to connect the or each externally-facing connection port in the ledge with the associated at least one receiving station fluid port.

In this aspect of the invention, the advantages of the rigid ledge arrangement of the vessel according to the first aspect described above become more readily apparent.

The means to connect may comprise means to urge the or each respective externally-facing connection port in the ledge towards the associated at least one receiving station fluid port to form a sealed connection. The urging means may comprise a clamp plate securable to the base to urge the vessel into the receiving station. The clamp plate may be securable to the base via thumb screws. Whereas in some embodiments a sufficient seal may be present by virtue of gravity urging the or each respective externally-facing connection port towards the associated at least one receiving station fluid port, a more reliable seal may be provided if an additional urging means is provided. Where there is no additional urging means, the means to connect may be considered as being the receiving station itself, in conjunction with the vessel, which combine to locate the vessel for registration of the respective ports.

The receiving station may include a plurality of vessel locations for receiving a corresponding plurality of bioreactor vessels, each vessel location having at least one said receiving station fluid port.

Where the urging means comprises a clamp plate, the clamp plate may be adapted to urge each of the plurality of vessels into the associated vessel location simultaneously. This enables the ports at each vessel to have their seals reinforced in a single action.

The system may further comprise a valve assembly having multiple fluid supplies, the valve assembly operable to supply a selected fluid to a selected receiving station fluid port in the base. In this manner, the fluid connection to each vessel is capable of delivering a selected one (or a mixture of) the fluid supplies to the vessel.

The system may include a plurality of said reactor vessels. The plurality of reactor vessels is formed as a cassette. By forming the vessels as a cassette, the vessels can all be inserted or removed from the vessel receiving stations as a unit. This would reduce vessel handling time.

According to a third aspect of the invention, there is provided a bioreactor system, including a cell culture module comprising:

a base including a receiving station for removably receiving a bioreactor vessel; and a bioreactor vessel having a chamber defined at least by bottom and side walls, and having a fluid port through one of the walls;

wherein the receiving station includes a fluid port, located such that the port in the vessel wall is in registration with the fluid port in the receiving station when the vessel is received in the receiving station, thereby defining a fluid flow path between the base and the vessel chamber.

In embodiments according to this aspect of the invention, rather than a rigid ledge to define the position of the externally-facing connection port so as to be in the correct location and orientation for registration with a corresponding port in a receiving station, the fluid port is positioned by virtue of its location through a wall of the vessel. As with the first and second aspects of the invention, the fluid pathway(s) between the vessel and the receiving station (for example) can be established simply on insertion of the vessel into the receiving station, without the need to make individual connections and without the contamination risk drawbacks discussed above with respect to the prior art clamp plate arrangement.

BRIEF DESCRIPTION OF THE DRAWINGS

The invention will be described, by way of example, with reference to the accompanying drawings, in which:

FIG. 2 is a top perspective view of a microscale bioreactor vessel for insertion into the cell culture module of FIG. 1;

FIG. 3 is a bottom perspective view of the bioreactor vessel of FIG. 2;

FIG. 3A is a bottom perspective view of a lid portion of the bioreactor vessel of FIGS. 2 and 3;

DETAILED DESCRIPTION

Microscale Bioreactor Vessels Embodiment

Figure 1:
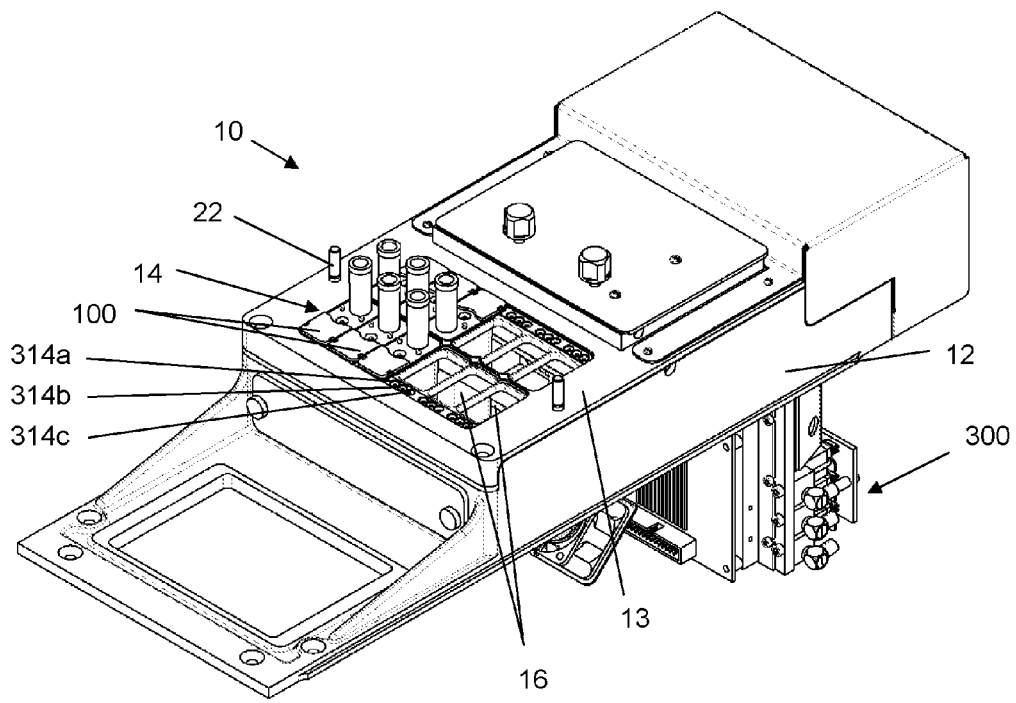
FIG. 1 is a perspective view from above of a portion of a microscale bioreactor system cell culture module.

A cell culture module 10 for processing an array of microscale bioreactors 100 is shown in FIG. 1. The cell culture module 10 forms part of a larger bioreactor processing system (not shown), and would typically be mounted to the deck of a base station in the system.

The cell culture module 10 comprises a base 12, to which is mounted a base plate 13 defining a receiving station 14 for removably receiving a plurality of bioreactor vessels 100. In the illustrated embodiment, the receiving station 14 can hold up to twelve vessels 100 in two rows of six at respective locations 16. In FIG. 1, six vessels 100 are shown in position in their respective vessel receiving locations 16, while six of the vessel receiving locations 16 are shown empty to better illustrate the fluid ports in the base plate 13 (as described below). It will be appreciated, however, that the receiving station 14 could be designed to accommodate a greater or lesser number of vessels 100 and that the vessels 100 could be arranged in any suitable configuration.

One or more heaters or chillers (not shown) may be located adjacent to the vessel receiving locations 16 to control the temperature of the vessels 100.

Figure 4:
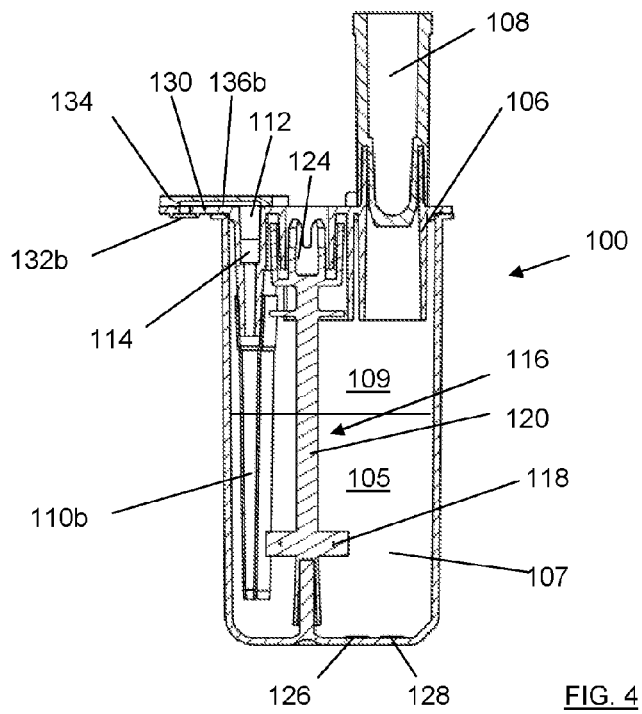
FIG. 4 is a cross-sectional view of the bioreactor vessel of FIGS. 2 and 3.

With reference to FIGS. 2 to 4 in particular, a microscale bioreactor vessel 100 for use with the cell culture module 10 comprises front, back, top, bottom and side walls 101a, 101b, 102, 103, 104a, 104b defining a chamber 105 for receiving a cell culture solution 107 having a headspace 109 above. The top wall 102 includes a pipette access port 106, on which is removably attached a cap 108. The cap 108 is removed for fluids to be pipetted into or out of the vessel 100. As best seen in FIG. 3A, the vessel further includes bank of three tubes 110a-c, each having an associated fluid input port 112a-c in the top wall 102 of the vessel. The fluid input ports 112a-c each include a filter 114.

A stirrer 116 comprising blades 118 mounted at the base of a vertical shaft 120 is rotatably mounted within the vessel 100. The upper end of the shaft 120 includes a drive input 124.

A pH sensor spot 126 and a DO sensor spot 128 are disposed on the bottom wall 103, such that they are able to detect the pH and DO levels of the solution 107 and to be interrogated from the exterior of the vessel 100.

Venting of the vessel chamber 105 is achieved via a labyrinthine path connecting the chamber 105 to atmosphere via the stirrer shaft drive input 124. Alternatively, a separate vent port may be provided towards the top of the vessel 100.

The top wall 102 of the vessel 100 includes a lip 130 projecting out to the side of the vessel, beyond the side wall 104a. The lip 130 includes three through ports 132a-c. A gallery plate 134 is secured above a portion of the top wall 102 including the lip 130 and includes three grooves 136a-c extending between the respective gas input ports 112a-c at the top of the tubes 110a-c and each of the associated through ports 132a-c, thereby defining a conduit between each of the ports and the vessel chamber 105 via the respective tube 110a-c. The lip 130 and gallery plate 134 together form a rigid ledge projecting to the side of the vessel. The top wall 102 including the lip 130 and associated gallery plate 134 may comprise a lid that is attached to the remainder of the vessel 100. Alternatively, the lip 130 may project directly from the side wall 104a, with the gallery plate 134 being a part of the top wall 102.

A valve assembly 300 is mounted to the underside of the cell culture module base 12. The valve assembly 300 is received in a cavity of the bed station when the cell culture module 10 is connected to the bed station.

Figure 14:
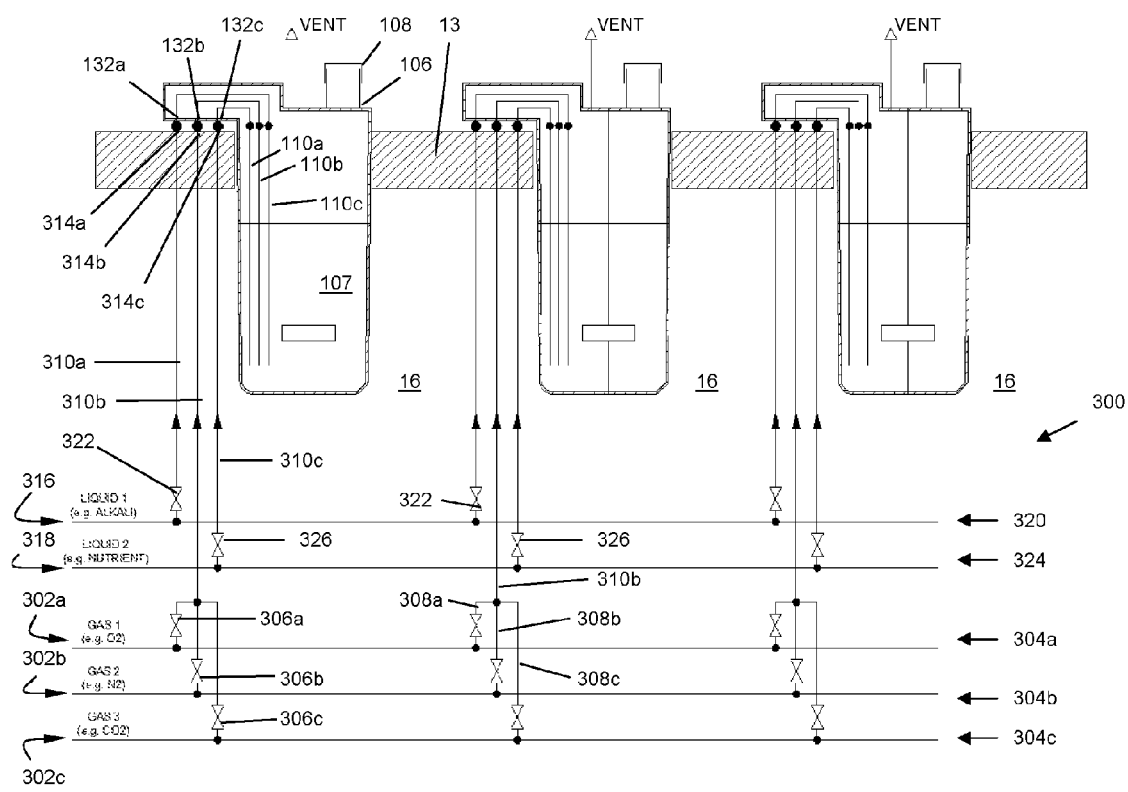
FIG. 14 is a schematic diagram of some of the fluid lines in the cell culture module of FIGS. 1 and 5.
Figure 6:
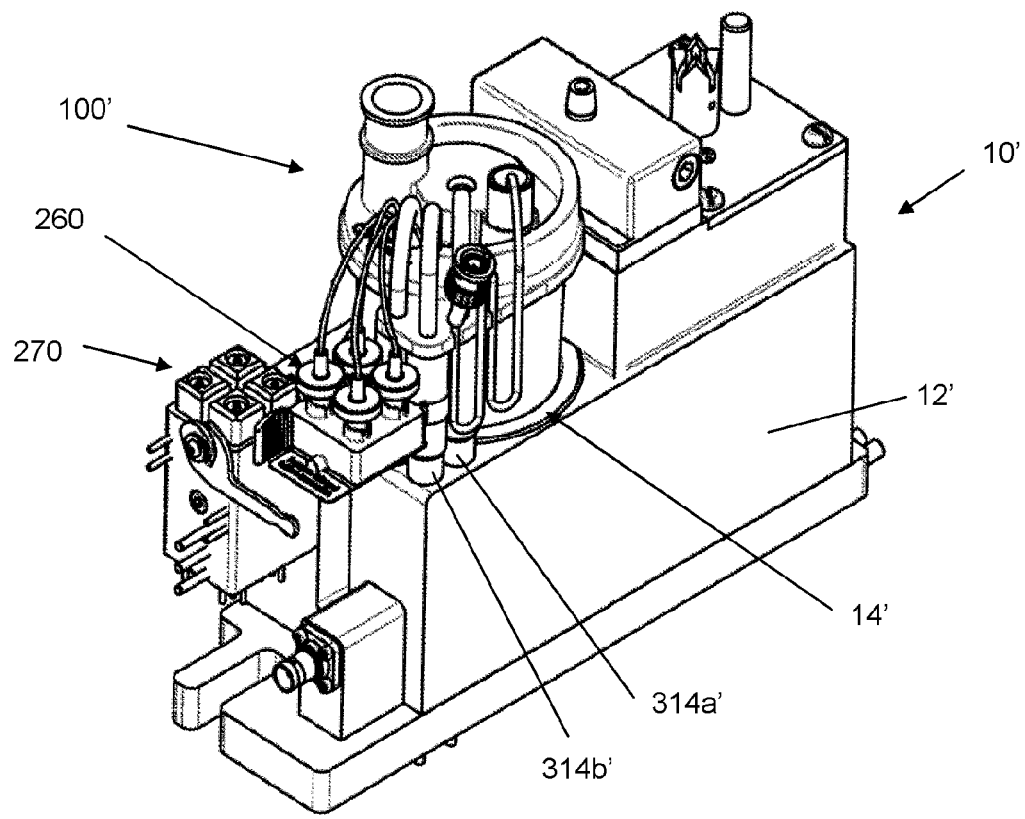
FIG. 6 is a perspective view from above of a portion of an alternative bioreactor system cell culture module.
Figure 6A:
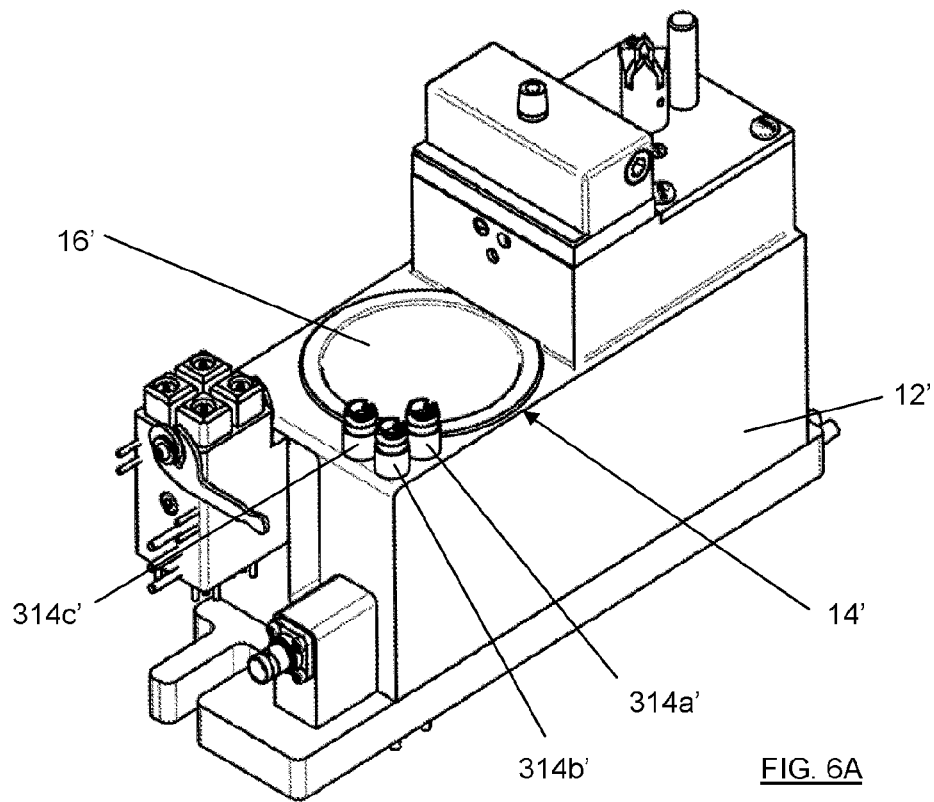
FIG. 6A corresponds to FIG. 6, but without a bioreactor vessel in place.
Figure 7:
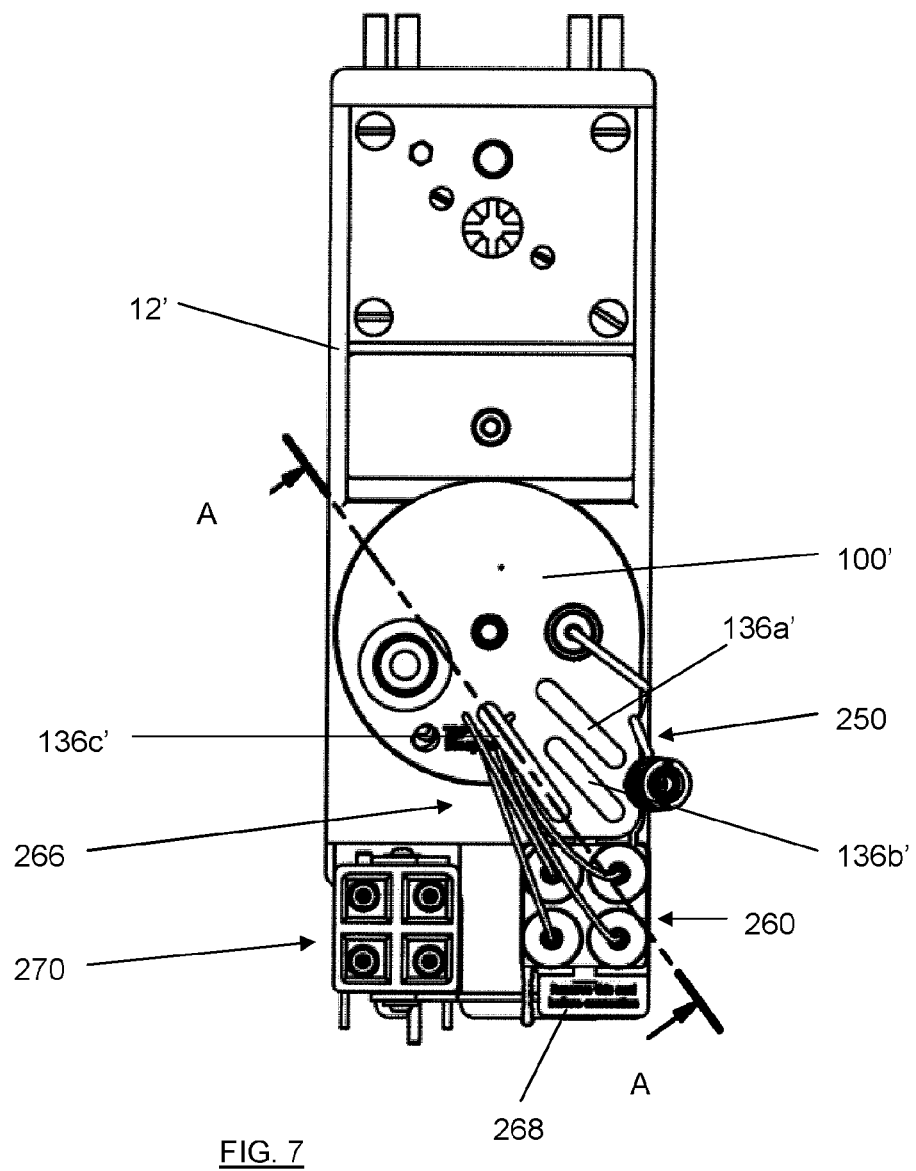
FIG. 7 is a top plan view of the cell culture module of FIG. 6.
Figure 8:
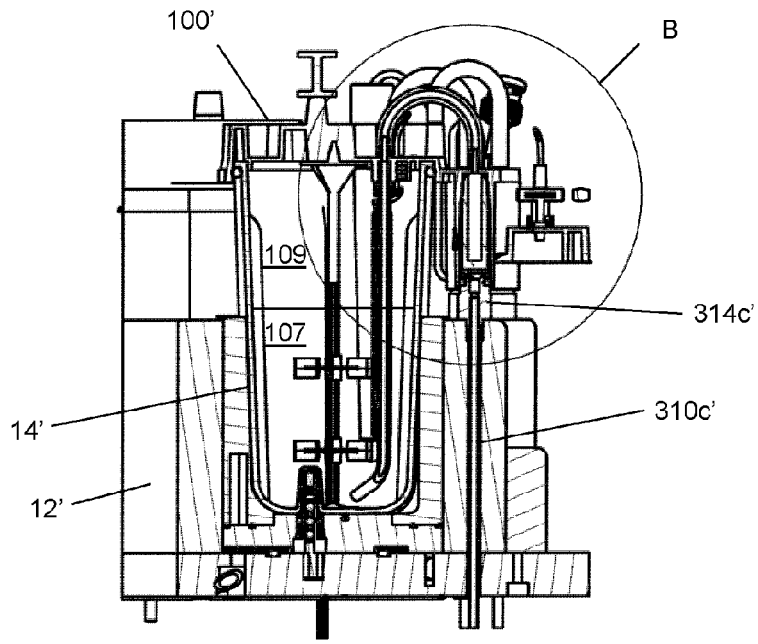
FIG. 8 is a cross-sectional view through A-A of FIG. 7.
Figure 9:
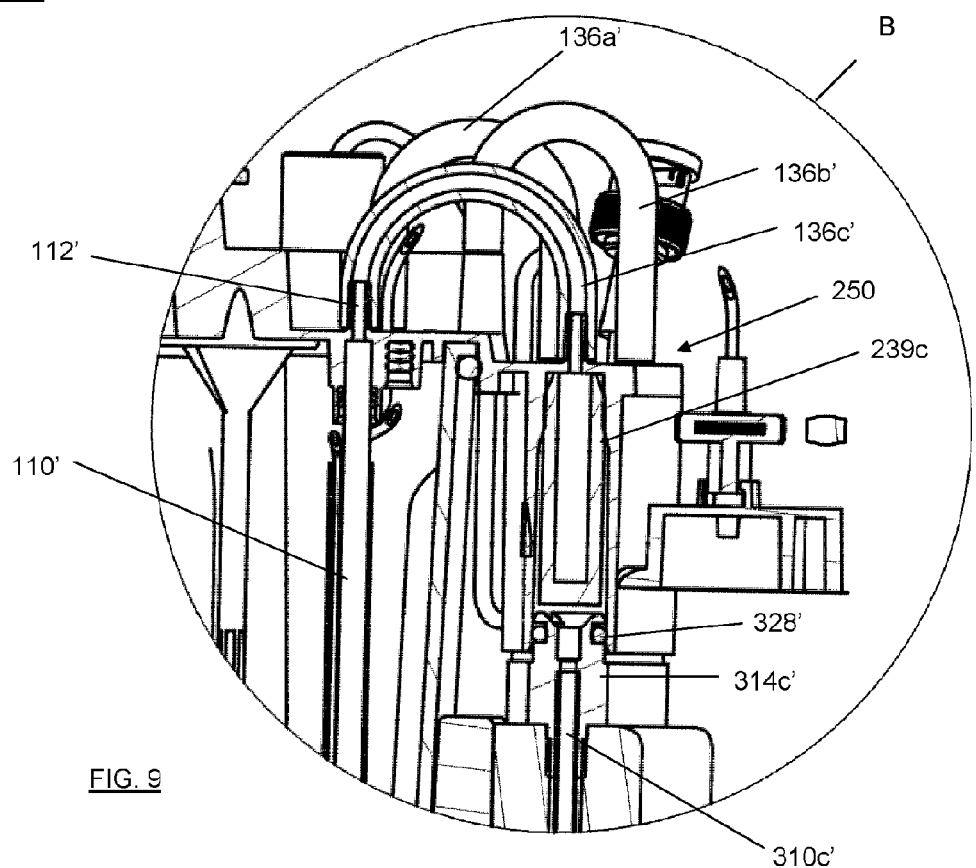
FIG. 9 is a detail view of portion B of FIG. 8, showing the interconnections between a bioreactor vessel and the cell culture module.
Figure 10:
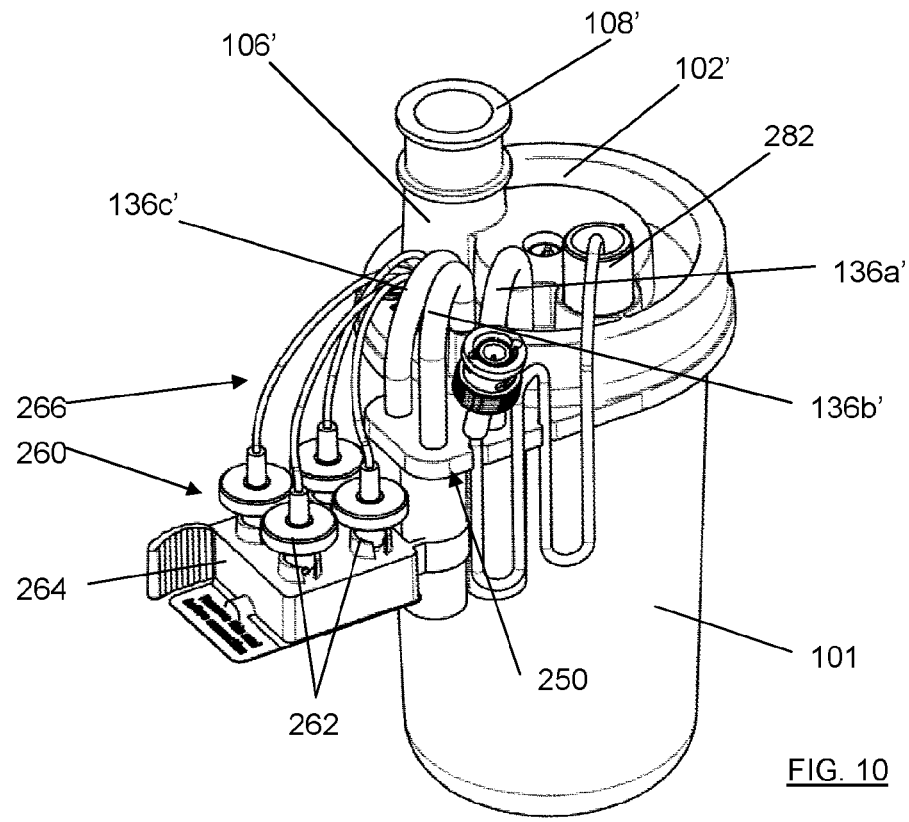
FIG. 10 is a top perspective view of a bioreactor vessel for insertion into the cell culture module of FIG. 6.
Figure 10A:
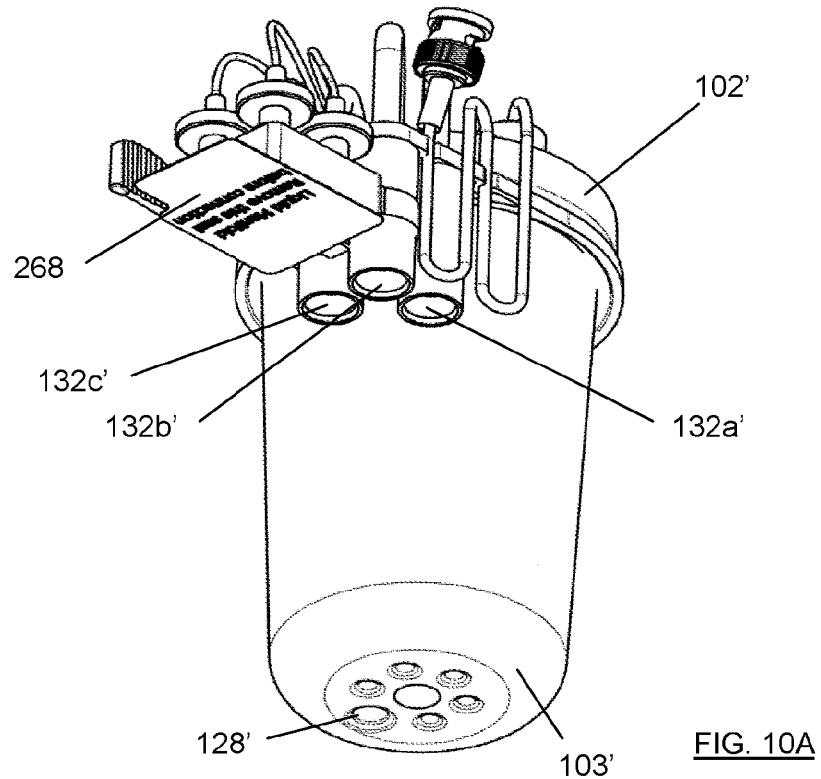
FIG. 10A is a bottom perspective view of the bioreactor vessel of FIG. 10.
Figure 11:
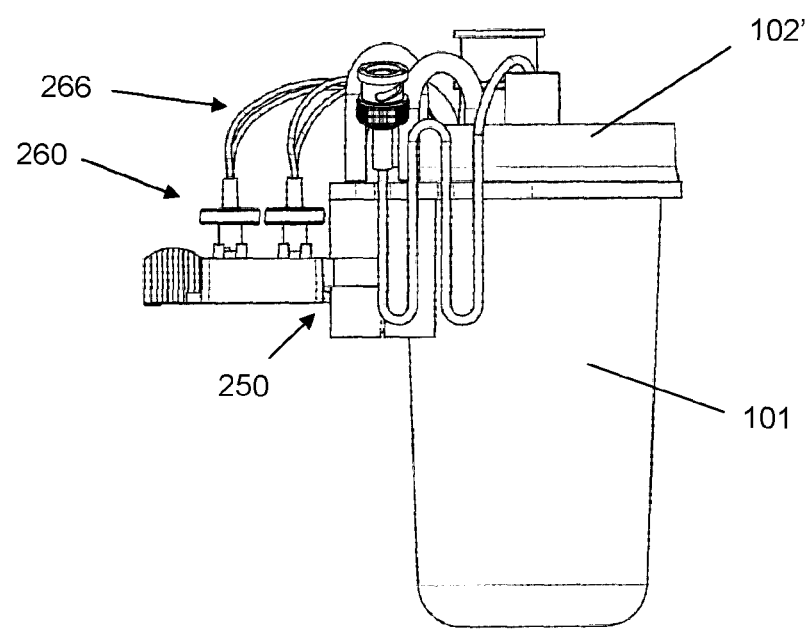
FIG. 11 is a side elevation of the bioreactor vessel of FIG. 10.

With reference also to FIG. 14, the valve assembly 300 has three gas input ports 302a-c, respectively connectable to $O_2$, $N_2$ and $CO_2$ gas supplies. A bank of valves 304a-c is associated with each respective input port 302a-c, each bank 304a-c comprising a valve 306a-c for each vessel receiving location 16. Thus, for the 12 vessel receiving locations 16 illustrated in FIG. 1, the valve assembly comprises a total of 36 gas input valves 306a-c.

From another point of view, each vessel receiving location 16 has three associated gas input valves: one (306a) to control the supply of $O_2$, another (306b) to control the supply of $N_2$ and another (306c) to control the supply of $CO_2$.

Each valve 306a-c has an outlet port to which is connected an output conduit 308a-c. The valves 306a-c are grouped according to the vessel receiving location 16 to which they correspond, and the output conduits 308a-c for each group are joined to a proximal end of a respective gas transport conduit 310b. There is therefore a gas transport conduit 310b associated with each vessel receiving location 16. The distal end of each gas transport conduit 310b is received in a conduit chamber 312 and is connected therein to a respective outlet port 314b on an upper surface of the base plate 13.

The valve assembly further includes first and second liquid inlet ports 316, 318, respectively connectable to first and second liquid supplies. By way of example, the first liquid connected to the first inlet port 316 may be an alkali, to control the pH level in the vessel, and the second liquid may be a nutrient feed. A bank of valves 320 is associated with the first input port 316, and comprises a valve 322 for each vessel receiving location 16. Thus, for the 12 vessel receiving locations 16 illustrated in FIG. 1, the valve assembly comprises a total of 12 first liquid input valves 322. A bank of valves 324 is associated with the second input port 318, and comprises a valve 326 for each vessel receiving location 16. Thus, the valve assembly comprises a total of 12 second liquid input valves 326.

Each first liquid input valve 322 has an outlet port to which is connected a first liquid transport conduit 310a. There is therefore a first liquid transport conduit 310a associated with each vessel receiving location 16. The distal end of each first liquid transport conduit 310a is received in the conduit chamber 312 and is connected therein to a respective outlet port 314a on an upper surface of the base plate 13.

Each second liquid input valve 326 has an outlet port to which is connected a second liquid transport conduit 310c. There is therefore a second liquid transport conduit 310c associated with each vessel receiving location 16. The distal end of each second liquid transport conduit 310c is received in the conduit chamber 312 and is connected therein to a respective outlet port 314c on an upper surface of the base plate 13.

There are therefore three fluid transport conduits associated with each vessel receiving location: a gas transport conduit 310b and a pair of liquid transport conduits 310a, 310c.

Figure 5:
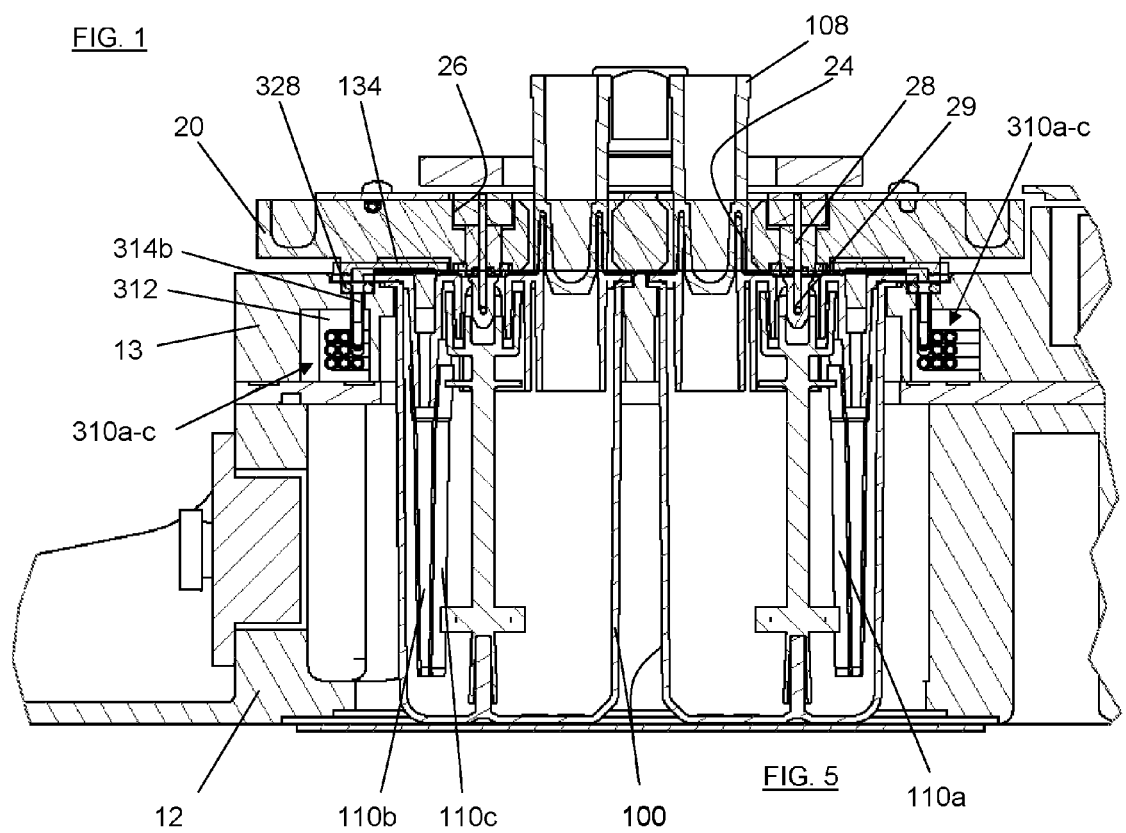
FIG. 5 is a cross-sectional view of a portion of the cell culture module of FIG. 1.

As best seen in FIG. 5, a clamp plate 20 is removably connected to the cell culture module base plate 13, in a position overlying the vessel receiving station 14, via a pair of posts 22 projecting from the upper surface of the base plate 13. The clamp plate 20 is removed in FIG. 1, for clarity. The clamp plate 20 is a generally rectangular, planar member having an array of relatively large circular apertures 24 arranged in two rows of six, in positions corresponding to the vessel receiving locations. As described below, these apertures 24 are to accommodate the upstanding pipette access ports 106, with or without the associated caps 108 attached, of respective vessels 100 when received in the respective vessel receiving locations 16.

Adjacent to each of the relatively large apertures 24 is a smaller circular hole 26. A shaft 28 is rotatably received in each of these smaller holes 26. The apertures 24 and the holes 26 all extend from top to bottom through the clamp plate 20. The underside of each shaft 28 has a drive element 29 for forming a drive connection with the drive input 124 of the stirrer 116 of a respective vessel 100.

Use of the Bioreactor Processing System

In order to carry out an experiment run, the cell culture station 10 is loaded up with vessels 100, each vessel being placed in a respective vessel receiving location within the receiving station 14.

When the vessels 100 are inserted into the receiving station 14, the ports 132a-c in the bottom surface of the lip 130 are aligned with and form a sealed connection with the corresponding receiving station fluid ports 314a-c on the upper surface of the base plate 13. The respective ports are automatically aligned with one another on insertion by virtue of the defined locations of the vessel receiving station, including the fluid ports 314a-c adjacent thereto, and the rigid ledge, which places the corresponding vessel connection ports 132a-c in registration with the receiving station fluid ports 314a-c.

An additional sealing member, such as an o-ring 328, may reinforce the seal. The weight of the vessel 100 and its contents alone may be sufficient to form a good seal between the externally-facing connection ports 132a-c and the respective receiving station fluid ports 164. However, the seals are preferably reinforced by application of a downward force from the clamp plate 20.

The clamp plate 20 is placed on top of the base plate 13 and secured in position via the posts 22. The vessel pipette access ports 106 and attached caps 108 project through the respective larger apertures 24 in the clamp plate 20.

In this manner, each vessel 100 is connected to each of the fluid supplies 302a-c, 316, 318 via the following path: gas (or fluid) supply 302a-c (or 316 or 318); valve assembly 300 via input port; through selectively opened valve 306a-c (or 322 or 326); via output conduit 308a-c (for the gas supplies) to transport conduit 310a-c; to receiving station fluid port 314a-c; to associated externally-facing connection port 132a-c in vessel; via associated fluid conduit 136a-c to the associated tube inlet port 112a-c; through tube 110a-c; and in to vessel chamber 105.

As the clamp plate 20 is placed over the base plate 13, a drive coupling is attached to form a drive connection to each of the shafts 28, for driving each of the vessel stirrers 116.

The vessels 100 may be supplied pre-loaded with cell culture solution. Alternatively, the vessels 100 may be supplied empty, the cell culture solution being inserted via the respective pipette access ports 106 once the vessels are received in their respective locations. That insertion may be carried out manually, or automatically by means of a robotic liquid handling station.

The vessels 100 may be provided in aseptic packaging. To minimise the risk of contamination, the insertion of the vessels 100 into the receiving station 14 may take place within a controlled environment. The controlled environment may, for example, be a biological safety cabinet, such as a laminar flow cabinet, which may be fitted with, for example, a HEPA filter to prevent biological material contaminating the cell culture.

Monitoring and Control

As an experiment run progresses, the cell culture solution in each vessel 100 develops and has different requirements for optimum growth and production of target proteins and/or antibodies. Accordingly, the input parameters do not remain fixed throughout the experiment run but instead follow a profile. For example, in early stages of development, the cell culture may require a slightly more alkali environment as compared to later developmental stages.

During an experiment run, each vessel is individually monitored for pH and DO via the interrogation of the respective sensor spots 126, 128.

The resultant data stream can be used as input to a control system for feedback control of the input parameters for the individual vessels 100. For example, the data from the pH sensor 126 can be used as an input to determine the quantity of $CO_2$ (or alkali or other liquid to control the pH) supplied to the individual vessels 100 with a view to keeping the pH within a predetermined profile.

The temperature of each culture station module 100 may also be monitored by an associated temperature sensor. The data from the temperature sensors can be used as input to the heater(s) or chillers to ensure that the vessels 100 in the corresponding culture station module are maintained at a predetermined temperature profile.

As mentioned in the introductory portion of this description, the objective of an experiment run is to determine which set of input parameters provides optimum results. Accordingly, each vessel 100 in the cell culture module 10 may be run with a slightly different set of parameters than the others. For example, different vessels 100 may be run with one or more of the following varied as compared to the other vessels: pH profile, $CO_2$ profile, dissolved oxygen profile, nutrients profile, temperature profile and stirring speed.

The effect of the variations is assessed by monitoring the cell culture solution, during and after the experiment run, to determine one or more of: cell count, cell viability, cell size, biomass, metabolites and biological molecules, such as the product titre, which may be a protein or antibody. In this way, the effects of the variations in the parameters at the different stages of the run may be evaluated. This is achieved by the aspiration and dispensing of samples to well plates or to a sample cup for analysis as discussed above.

The best set of parameters may then be used as a reference point for further experiment runs.

Alternative Embodiments

Rather than being integral with the clamp plate 20, the drive mechanism may be mounted separately from the clamp plate 20.

Alternatively, in another embodiment, the drive connection between the drive mechanism and the stirrers 116 of the individual vessels 100 is established directly, without the intermediary of the clamp plate 20. In this embodiment, the stirrer shafts 120 may be longer than those of the preceding embodiments and be received in the respective smaller holes 26 in the clamp plate 20. Alternatively, the clamp plate 20 could be omitted altogether in this embodiment.

Rather than the grooves 136*a-c* in the gallery plate 134 defining three distinct and separate conduits, the gallery plate may instead define a manifold, having a branch to each respective externally-facing connection port 132*a-c* stemming from a main conduit which is connected to the vessel chamber 105, for example via a single tube 110.

Another alternative is for the three distinct inputs to merge before the vessel 100. One such arrangement would be for the fluid transport conduits 310*a-c* to merge to a single receiving station fluid port 314 on the upper surface of the base plate 13, for connection to a corresponding single externally-facing connection port 132 in the lip 130.

Instead of each of $O_2$, $N_2$ and $CO_2$ being supplied via the valve assembly 300, just a selected two of those gases could be supplied. For example, just $O_2$ and $N_2$ can be supplied. As discussed above, the $CO_2$ is provided to maintain the pH levels within a predetermined profile for mammalian cell cultures. However, that could be achieved in other ways, such as by dispensing, e.g., bicarbonate of soda or ammonia into the vessel contents. Accordingly, with such alternate pH level control, the $CO_2$ supply could be omitted and the pH be controlled by alkali or acid liquid addition. Where just two gases are supplied, the valve assembly of course only requires two banks 304 of gas valves.

Instead of a mixture of $O_2$ and $N_2$ being used to control the dissolved oxygen concentration in the cell culture solution, a combination of $O_2$ and air, or a combination of air and $N_2$ could be used. Also the $O_2$ gas could be provided for example as 50% $O_2$ and then mixed with either air or $N_2$.

In fact, it is conceivable that just a single gas or even no gas at all could be supplied. For example, it is known to rely on the diffusion of ambient air to supply $O_2$ and $N_2$ to the system. However, such a system would not be representative of a full-scale process, because such full-scale processes almost invariably have at least one gas supply.

More than three gases could be supplied, in which case an additional bank of valves and associated output conduits for each additional gas would be needed.

The $O_2$, $N_2$ and $CO_2$ connections have been described in terms of gas input connections. It will be appreciated that these input(s) could instead be in liquid form. Moreover, it will be appreciated that one or more of the fluid paths could be reversed, with the ports in the vessel being outlet ports, and fluid being extracted from the vessel via the fluid connections. That extraction could be for monitoring the contents of the vessel, be that the gases in the headspace 109 or the cell culture solution 107, the fluid connection taking the extracted samples for analysis. Such monitoring via the cell culture module 10 may replace the methods described above for aspirating samples via the pipette access port 106 for analysis. In one particular embodiment, a fluids circulation loop may be formed by having one of the ports in the vessel as an outlet port, and another port in the vessel being an input port. The fluids circulation loop may include one or more of: an external pump, a filter—for example a tangential flow filter, an oxygenating membrane, a gas exchanger, a heat exchanger, and a sampling device.

The vessels 100 have been described as having a three inlet (or outlet) ports 112*a-c* to the chamber 105, but it will readily be understood that more or fewer ports could be provided, with appropriate modifications being made to the associated fluid connections in the gallery plate 134 and the remainder of the cell culture module 10.

The drive connection to the respective stirrers has been described in terms of a mechanical connection. It will be understood that it is also possible to transmit the drive non-mechanically, such as by electromagnetic forces. For example, as a simple substitution, the driven element may comprise a magnet or a ferromagnetic element and the drive element may comprise a respective complementary ferromagnetic element or magnet, drive motion being conveyed via ferromagnetic forces between the respective magnet and ferromagnetic element.

A heater and or a chiller could be supplied for each vessel 100, in which case the temperature within individual vessels could be controlled via associated feedback control. Thus, the temperature profiles of different vessels could be varied relative to one another.

In order to prevent condensation in the upper portions of the vessels 100, heaters may be located near those upper portions, for example within the clamp plate 20 or in the region of the upper surface of the base plate 13.

As described, the tubes 110a-c extend to the bottom of the vessel 100 to supply gases directly into the cell culture solution 107. It will be understood, however, that the gas tube 110b (also known as a sparge tube) could be shorter, just extending into the headspace 109 to supply gases into the headspace, which gases would then diffuse into the cell culture solution. In fact, the tube 110b could be omitted entirely, with gases being supplied directly into the headspace 109 via the port 112b. For the liquid supplies, it is preferable for the tubes 110a,c to extend into the cell culture solution 107 so that the input fluids can be diffused at a steady state rate into the solution. Otherwise, with liquid supplies into the headspace, the liquid gathers into a droplet at the input port, dropping into the solution below only once the droplet has reached a certain size. This results in uneven and imprecise supply of the liquid into the solution, and fluctuations in the conditions therein.

Rather than or as well as the pH and DO sensor spots 126, 128, alternative sensors could be used. Examples include sensors for detecting: the $CO_2$ concentration, the temperature, cell count, cell viability, cell size, biomass, metabolites and biological molecules.

Also, rather than being detected remotely, for example by fluorescent effects, the parameters could be detected more directly by a probe inserted into the cell culture solution and/or into the headspace. Such a probe could be integral with the vessel 100 or could be attached to the clamp plate 20.

Another alternative sensing means could comprise an IC chip located within the vessel 100 and having contacts either within the vessel for connecting with an interrogating probe or accessible through a wall, to transmit signals directly from the chip.

Alternative Bioreactor Vessels Embodiment

FIGS. 6 to 13 illustrate an alternative implementation of the invention, applied to larger scale bioreactor vessels 100' than the microscale bioreactor vessels 100. To assist in recognising the parallels between the embodiments, where possible analogous features will be referenced with similar reference signs to those of the microscale embodiment, but suffixed with a prime (').

A cell culture module 10' for processing a single bioreactor 100' is shown in FIGS. 6 to 9. The cell culture module 10' forms part of a bioreactor processing system (not shown), and would typically be mounted to the deck of a base station in the system. Unless otherwise described, the bioreactor 100' and associated cell culture module 10' operate analogously to the microscale embodiment, with appropriate modifications.

The cell culture module 10' comprises a base 12', having a top surface defining a receiving station 14' for removably receiving the bioreactor vessel 100'. It will be appreciated, however, that the receiving station 14' could be designed to accommodate a greater number of vessels 100', with suitable adaptation.

One or more heaters/chillers (not shown) may be located adjacent to the vessel receiving location 16' to control the temperature of the vessel 100'.

With reference to FIGS. 10 to 13A in particular, a bioreactor vessel 100' for use with the cell culture module 10' comprises a vessel body portion 101 defining a chamber 105' for receiving a cell culture solution 107' having a headspace 109' above. The vessel typically holds a working volume of approximately 200 to 250 ml of cell culture solution 107'. It will be understood, however, that the principles described with reference to this scale of vessel may be applied, mutatis mutandis, to both larger- and smaller-scale vessels.

The vessel further comprises a lid portion 102' secured to the top of the body portion 101 by a friction fit between a skirt 212 overlapping a circumferential lip 214 on the upper edge of the vessel body portion 101. An O-ring 216 is retained between the skirt 212 and an outer wall below the lip 214 to provide a seal between the lid portion 102' and the body portion 101. The lid portion 102' includes a pipette access port 106', on which is removably attached a cap 108'. A sparge tube 110' has a distal end opening in the cell culture solution 107' and a proximal end terminating at a port 112' through the lid portion 102'. A gas input line 136c' is connected at one end to the port 112' and at the other end to a fluids module 250 and may include a filter (239c).

A stirrer 116' comprising blades 118' mounted at the base of a vertical shaft 120' is rotatably mounted within the vessel 100'. The upper end of the shaft 120' includes a drive input 124', and is retained within the lid portion 102' by means of a labyrinth seal arrangement.

The vessel includes a DO sensor spot 128' disposed on a bottom wall 103' of the body portion 101' to detect the DO levels of the solution and to be interrogated from the exterior of the vessel 100'.

For mammalian cell cultures, a pH sensor spot (not shown) such as described in the microscale embodiment can be used for monitoring the pH level of the medium. However, for microbial cell cultures, which may directly affect the accuracy of a pH spot, the vessel can include a pH electrode sensor probe 280 received in a port 282 in the lid portion 102'. A distal end 284 of the electrode probe 280 extends into the vessel chamber 105' so as to be covered, in use, by the cell culture medium 107' for monitoring the pH level of the medium in a known manner.

The fluids module 250, in addition to the gas input line 136c' to the sparge tube 110', includes a further gas line 136a'. Gas line 136a' is a second input line, connected to a port 235 through the lid portion 101' for delivery of gases into the headspace 109'. This input line 136a' may also include a filter (239c).

The fluids module 250 may be respectively connectable to $O_2$, $N_2$ and $CO_2$ gas supplies for selective controlled delivery of those gases, alone or in combination, to the vessel via the input lines 136a' and 136c'.

Figure 12:
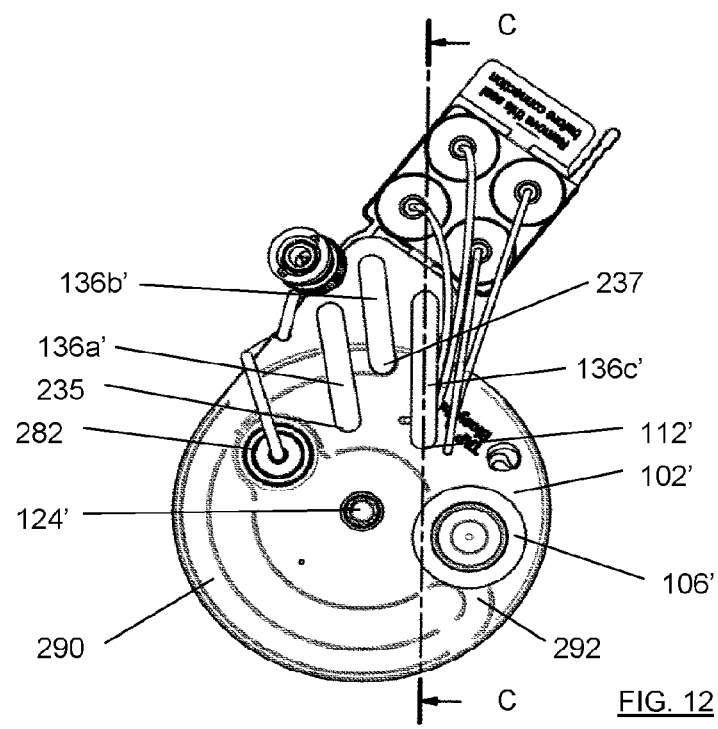
FIGS. 12 and 12A are top plan views of the bioreactor vessel of FIG. 10.
Figure 13:
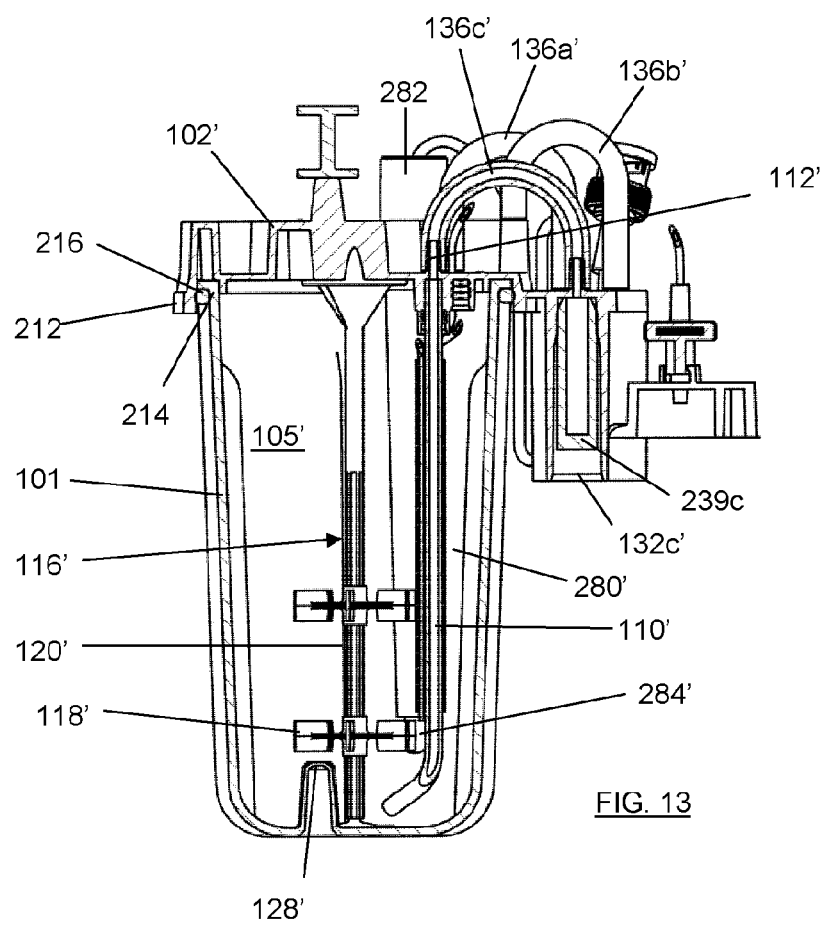
FIG. 13 is a cross-sectional view through C-C of FIG. 12.
Figure 12A:
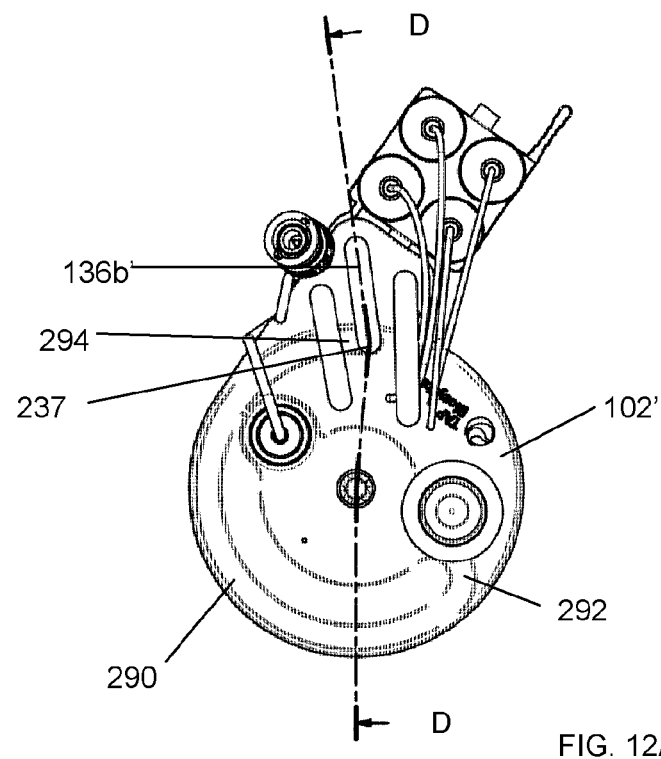
Figure 13A:
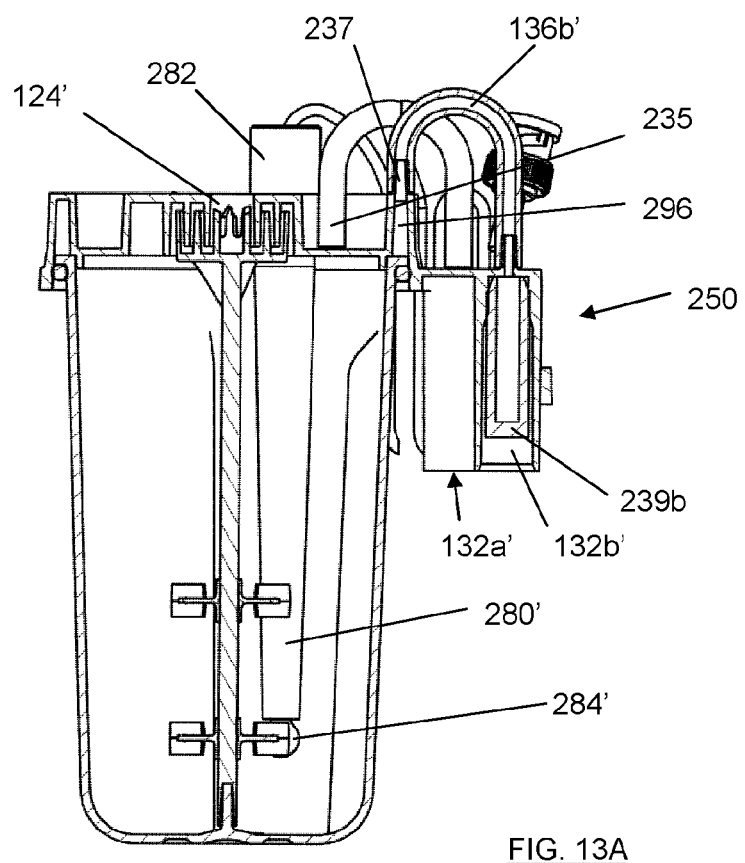
FIG. 13A is a cross-sectional view through D-D of FIG. 12A.

Referring in particular to FIG. 12, the lid portion 101' includes an arcuate groove 290 in a lower surface thereof. The groove 290 extends circumferentially around approximately 250° of the perimeter of the lid portion from a first end 292 to a second end 294. The groove 290 sits on top of a flat surface on the lip 214 of the vessel body portion 101 to define a circumferentially arranged conduit 296 (see FIGS. 12, 12A). At the first end 292 of the groove, there is an enlarged opening that provides a fluid communication with the vessel chamber 105' for the outlet passage of fluids evaporated from the headspace 109' into the conduit 296.

An outlet line 136b' is connected at the second end 294 of the groove, for the passage of the evaporated outlet fluids to the fluids module 250. This outlet line 136b' may also be provided with a filter 239b, and is typically connected to sensors (not shown) for monitoring the gas and water content of the outlet fluid to provide an indicator of metabolic activity in the cell culture, as described in the introductory portion of the description.

Venting of the vessel chamber 105' is achieved via a separate vent port provided towards the top of the vessel 100'. Alternatively, venting may be achieved, as in the microscale embodiment, by means of a labyrinthine path connecting the chamber 105' to atmosphere via the stirrer shaft drive input 124'.

The fluids module 250 forms an integral part of the top wall 102' of the vessel 100', comprising a rigid ledge projecting out to the side of the vessel, beyond the body portion 101. The fluids module 250 defines three through ports. The flexible conduits 136a-c' are connected to respective top ends of the through ports, which respectively terminate at their bottom ends at connection ports 132a-c', thereby defining a conduit between each of the connection ports 132a-c' and the vessel chamber 105'. The filters 239a-c are contained within the through ports.

The top wall 102' including the fluids module ledge 250 may comprise a lid that is attached to the remainder of the vessel 100'. Alternatively, the fluids module ledge 250 may project directly from the body portion 101.

A valve assembly (not shown) is mounted to the underside of the cell culture module base 12'. The vessel receiving location has three associated valves: one to control the supply of $O_2$, another to control the supply of $N_2$ and another to control the supply of $CO_2$, each for delivery to the conduit 136c' for delivery to the vessel chamber 105' via the sparge tube 110'. Further valves are included to control the supply of fluids (typically gases) through the other conduits 136a' and 136b'.

Each valve has an outlet port (not shown) to which is connected a proximal end of a respective transport conduit 310a-c' through the base 12'. The distal end of each transport conduit 310a-c' is in fluid connection with a respective receiving station outlet port 314a-c' on the upper surface of the base 12'.

The vessel 100' further includes a liquids module 260 comprising four spigots 262 upstanding on a rigid platform 264, each in fluid connection with the vessel chamber 105' via respective flexible conduits 266. A protective foil 268 is secured to the underside of the platform 264.

Use of the Macro-Scale Bioreactor Processing System

In order to carry out an experiment run, the cell culture station 10' is loaded up by placing a vessel 100' in the vessel receiving location 16' within the receiving station 14'.

When the vessel 100' is inserted into the receiving station 14', the ports 132a-c' in the bottom surface of the fluids module ledge 250 are aligned with and form a sealed connection with the corresponding receiving station fluid ports 314a-c' upstanding from the upper surface of the base 12'. The respective ports are automatically aligned with one another on insertion by virtue of the defined locations of the vessel receiving station, including the fluid ports 314a-c' adjacent thereto, and the rigid ledge 250, which places the corresponding vessel connection ports 132a-c' in registration with the receiving station fluid ports 314a-c'.

An additional sealing member, such as an o-ring 328', may reinforce the seal. The weight of the vessel 100' and its contents alone may be sufficient to form a good seal between the externally-facing connection ports 132a-c' and the respective receiving station fluid ports 314a-c'. However, the seals are preferably reinforced by application of a downward force from a clamp plate (not shown).

In addition to the 'automatic' formation of the gas connections between the vessel 100' and the receiving station fluid ports 314a-c' via the rigid fluids module 250, the liquid connection can be established by manually connecting the platform 264 over a corresponding connection module 270 on the base 12', after having removed the protective foil 268.

The vessel 100' may be supplied pre-loaded with cell culture solution. Alternatively, the vessel 100' may be supplied empty, the cell culture solution being inserted via the fluid transfer port 106' once the vessel is received in the receiving station 14'. That insertion may be carried out manually, or automatically by means of a robotic liquid handling station.

The vessel 100' may be provided in aseptic packaging. To minimise the risk of contamination, the insertion of the vessel 100' into the receiving station 14' may take place within a controlled environment. The controlled environment may, for example, be a biological safety cabinet, such as a laminar flow cabinet, which may be fitted with, for example, a HEPA filter to prevent biological material contaminating the cell culture.

Monitoring and Control of the Macro-scale System

As an experiment run progresses, the cell culture solution in the vessel 100' develops and has different requirements for optimum growth and production of target proteins and/or antibodies. Accordingly, the input parameters do not remain fixed throughout the experiment run but instead follow a profile. For example, in early stages of development, the cell culture may require a slightly more alkali environment as compared to later developmental stages.

During an experiment run, the vessel 100' is monitored for pH and DO via the interrogation of the sensor spot 270 and via the pH probe 280.

The resultant data stream can be used as input to a control system for feedback control of the input parameters for the vessel 100'. For example, the data from the pH probe 280 can be used as an input to determine the quantity of $CO_2$ supplied to the vessel 100' with a view to keeping the pH within a predetermined profile.

The temperature of the culture station module 10' may also be monitored by an associated temperature sensor. The data from the temperature sensor can be used as input to the heater(s) to ensure that the vessel 100' in the culture station module 10' is maintained at a predetermined temperature profile.

Alternative Embodiments

Rather than comprising upstanding projections from the upper surface of the base 12', the receiving station fluid ports 314a-c' may be flush with that upper surface. In this case, the o-rings 328' may be placed into annular recesses in that upper surface to act as face seals instead of circumferential seals.

The liquid connections may be established 'automatically' too, by forming the liquids module 260 as a rigid extension of the vessel 100', instead of being secured thereto just via the flexible conduits 266, so as to be aligned with the mating connection module 270 on insertion of the vessel 100' into the receiving station 14'.

Vertical Ports Embodiments

In another embodiment, which is not illustrated, rather than being disposed on a horizontal surface of the base 12' or base plate 13, the receiving station fluid ports 314a-c(') may be disposed on a substantially vertical sidewall of the receiving station 14, 14'. With such an arrangement, the externally-facing connection ports 132a-c(') on the vessel will be through a side wall 101a,b; 104a,b of the vessel. The fluid connection will be established as the vessel is placed in the receiving station by virtue of cooperating features of the vessel and the receiving station—such as the bottom wall of the vessel in conjunction with the bottom of the receiving station defining the height of the fluid connections, and the respective side walls defining the lateral locations thereof. With tapering side walls, the weight of the vessel and contents may be sufficient to form a sealed connection. However, additional lateral force may be applied, for example via clamping means, to reinforce the seal.

The invention claimed is:

1. A bioreactor vessel for removable connection to a bioreactor module, the vessel comprising:
   a chamber defined by top, bottom and side walls;
   a rigid ledge projecting to a side of the vessel and having defined therein a through port which extends through the rigid ledge in a direction which is substantially perpendicular to the direction of projection of the rigid ledge and which terminates at one end at an externally-facing connection port;
   a conduit at least partly defining a fluid flow path between the chamber and the externally-facing connection port, a chamber end of the conduit being in fluid communication with the chamber and the other end of the conduit being connected to the through port; and
   a gallery plate, wherein the gallery plate includes a groove extending between the externally-facing connection port and the chamber, thereby defining said conduit.

2. The vessel of claim 1, wherein the chamber includes a chamber port through one of said top, bottom and side walls, the conduit being connected at the chamber end to said chamber port.

3. The vessel of claim 2, wherein the ledge comprises a part of the top wall of the chamber, which also defines the chamber port.

4. The vessel of claim 3, wherein the top wall comprises a lid of the vessel.

5. The vessel of claim 2, wherein the ledge comprises a part of a side wall of the chamber.

6. The vessel of claim 1, wherein the ledge comprises a part of a side wall of the chamber and the gallery plate comprises a part of the top wall of the chamber, which also defines the chamber port.

7. The vessel of claim 1, wherein the conduit is defined externally of the ledge.

8. The vessel of claim 7, wherein the conduit comprises flexible tubing.

9. The vessel of claim 1, wherein said other end of the conduit is connected at an opposite end of the through port to that of the externally facing connection port.

10. A bioreactor vessel for removable connection to a bioreactor module, the vessel comprising:
    a chamber defined by top, bottom and side walls;
    a rigid ledge projecting to a side of the vessel and having an externally-facing connection port which faces substantially perpendicular to the direction of projection of the rigid ledge; and
    a conduit at least partly defining a fluid flow path between the chamber and the externally-facing connection port, a chamber end of the conduit being in fluid communication with the chamber and the other end of the conduit being connected to the externally-facing connection port,
    wherein the conduit is defined internally within the ledge; and
    wherein the externally facing connection port is disposed relative to the bioreactor vessel to enable automatic and direct connection to a fluid port in a receiving station of the bioreactor module when the bioreactor vessel is provided in the receiving station;
    wherein the ledge comprises:
    a lip projecting to a side of the vessel; and
    a gallery plate;
    wherein the externally-facing connection port extends through the lip, and wherein the gallery plate includes a groove extending between the externally-facing connection port and the chamber, thereby defining said conduit.

11. The vessel of claim 10, wherein the chamber includes a chamber port, the conduit being connected at the chamber end to said chamber port, wherein the lip comprises a part of the top wall of the chamber, which also defines the chamber port.

12. The vessel of claim 11, wherein the top wall comprises a lid of the vessel.

13. The vessel of claim 11, wherein the lip comprises a part of a side wall of the chamber, and wherein the gallery plate comprises a part of the top wall of the chamber, which also defines the chamber port.

14. The vessel of claim 10, wherein the ledge projects from an upper end of the vessel.

15. The vessel of claim 10, wherein the externally-facing connection port is on a bottom surface of the ledge.

16. The vessel of claim 10, wherein the ledge includes a plurality of said externally-facing connection ports, a respective plurality of conduits at least partly defining a respective plurality of fluid flow paths between the chamber and each of said externally-facing connection ports.

17. The vessel of claim 16, wherein the plurality of flow paths comprises a manifold, having a branch to each respective externally-facing connection port stemming from a main conduit.

18. The vessel of claim 10, wherein the vessel further comprises a tube, an upper end of the tube being connected to the chamber end of the conduit.

19. A bioreactor system, including a cell culture module comprising:
    a base including a receiving station which has the bioreactor vessel of claim 10 removably received therein, the receiving station including at least one receiving station fluid port, such that the or each externally-facing connection port in the ledge is in registration with an associated at least one receiving station fluid port when received in the receiving station; and
    means to connect the or each externally-facing connection port in the ledge with the associated at least one receiving station fluid port.

20. The system of claim 19, wherein the means to connect comprises means to urge the or each respective externally-facing connection port in the ledge towards the associated at least one receiving station fluid port to form a sealed connection.

21. The system of claim 20, wherein the urging means comprises a clamp plate securable to the base to urge the vessel into the receiving station.

22. The system of claim 21, wherein the clamp plate is securable to the base via thumb screws.

23. The system of claim 19, wherein the receiving station includes a plurality of vessel locations for receiving a corresponding plurality of bioreactor vessels, each vessel location having at least one said receiving station fluid port.

24. The system of claim 23, wherein the urging means comprises a clamp plate securable to the base to urge the vessel into the receiving station and the clamp plate is adapted to urge each of the plurality of vessels into the associated vessel location simultaneously.

25. The system of claim 19, further comprising a valve assembly having multiple fluid supplies, the valve assembly operable to supply a selected fluid to a selected receiving station fluid port in the base.

26. The system of claim 19, wherein the system includes a plurality of said reactor vessels.

27. The system of claim 26, wherein the plurality of reactor vessels is formed as a cassette.

\* \* \* \* \*